United States Patent
Schibli et al.

(10) Patent No.: US 11,806,142 B2
(45) Date of Patent: Nov. 7, 2023

(54) METHOD FOR THE MANUFACTURE OF PRECIOUS METAL ELECTRODES

(71) Applicant: Heraeus Deutschland GmbH & Co. KG, Hanau (DE)

(72) Inventors: Stefan Schibli, Hanau (DE); Robert Sievi, Hanau (DE); David Meder, Hanau (DE); Andreas Reisinger, Hanau (DE); Jens Trötzschel, Hanau (DE); Anna Fuchs, Hanau (DE); Heiko Specht, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 17/117,890

(22) Filed: Dec. 10, 2020

(65) Prior Publication Data

US 2021/0177323 A1    Jun. 17, 2021

(30) Foreign Application Priority Data

Dec. 13, 2019    (DE) ............. 10 2019 219 615.2

(51) Int. Cl.
*A61B 5/1486* (2006.01)
*C23C 18/06* (2006.01)
(Continued)

(52) U.S. Cl.
CPC .......... *A61B 5/14865* (2013.01); *C23C 18/06* (2013.01); *C23C 18/08* (2013.01); *A61B 5/14532* (2013.01); *A61B 2562/125* (2013.01)

(58) Field of Classification Search
CPC .......... C23C 18/06; C23C 18/08; A61N 1/04; C07F 15/0086
See application file for complete search history.

(56) References Cited

U.S. PATENT DOCUMENTS

| | | |
|---|---|---|
| 5,100,702 A | 3/1992 | Maeda et al. |
| 5,494,562 A | 2/1996 | Maley et al. |
| (Continued) | | |

FOREIGN PATENT DOCUMENTS

| | | |
|---|---|---|
| DE | 60125174 | 10/2007 |
| DE | 102006029947 | 1/2008 |
| (Continued) | | |

OTHER PUBLICATIONS

Hemmerich, Accelerated Aging—General Aging Theory and Simplified Protocol for Accelerated Aging of Medical Devices, Medical Plastics and Biomaterials Magazine, 1998.
(Continued)

*Primary Examiner* — Robert A Vetere
(74) *Attorney, Agent, or Firm* — Dicke, Billig & Czaja, PLLC

(57) ABSTRACT

One aspect relates to a method for the manufacture of a medical electrode, including: (i) providing a substrate; (ii) applying a composition onto the substrate, wherein the composition comprises (a) a non-aqueous solvent and (b) an organic precious metal complex compound that is dissolved in the solvent; (iii) heating the composition and thereby forming a precious metal layer on the substrate, wherein the solubility of the organic precious metal complex compound in propylene glycol mono-propyl ether at 25° C. and 1013 hPa is at least 1 mass percent, or at least 2, 3, 4, 5 or 10 mass percent, in relation to the total mass of the composition.

13 Claims, 2 Drawing Sheets

(51) Int. Cl.
*C23C 18/08* (2006.01)
*A61B 5/145* (2006.01)

(56) References Cited

U.S. PATENT DOCUMENTS

| | | | |
|---|---|---|---|
| 6,113,448 | A | 9/2000 | Kobayashi et al. |
| 6,457,408 | B1 | 10/2002 | Yanagisawa et al. |
| 6,728,092 | B2 | 4/2004 | Hunt et al. |
| 6,781,506 | B2 | 8/2004 | Schemenaur et al. |
| 6,830,778 | B1 | 12/2004 | Schulz et al. |
| 7,977,240 | B1 | 7/2011 | Rockenberger et al. |
| 8,066,805 | B2 | 11/2011 | Chandra et al. |
| 8,075,969 | B2 | 12/2011 | Anderson et al. |
| 8,389,444 | B2 | 3/2013 | Baecker |
| 9,096,051 | B1 | 8/2015 | Fohrenkamm et al. |
| 9,893,366 | B2 | 2/2018 | Kojima et al. |
| 10,364,500 | B2 | 7/2019 | Shukla et al. |
| 2002/0019658 | A1* | 2/2002 | Munshi .......... A61N 1/375 607/121 |
| 2005/0081907 | A1 | 4/2005 | Janora et al. |
| 2006/0093732 | A1 | 5/2006 | Schut et al. |
| 2007/0141838 | A1 | 6/2007 | Hsiao et al. |
| 2007/0207565 | A1 | 9/2007 | Kodas et al. |
| 2008/0046080 | A1* | 2/2008 | Vanden Bulcke ... A61N 1/0541 257/692 |
| 2010/0136785 | A1 | 6/2010 | Hsiao et al. |
| 2010/0305673 | A1 | 12/2010 | Jolly et al. |
| 2012/0264598 | A1 | 10/2012 | Carpenter et al. |
| 2012/0296350 | A1 | 11/2012 | Kar et al. |
| 2013/0156971 | A1* | 6/2013 | McCullough .......... C09D 11/52 427/532 |
| 2014/0087141 | A1 | 3/2014 | Wu et al. |
| 2014/0235011 | A1 | 8/2014 | Brown et al. |
| 2015/0125596 | A1 | 5/2015 | Ramakrishnan et al. |
| 2018/0208790 | A1 | 7/2018 | McCullough et al. |
| 2018/0362547 | A1 | 12/2018 | Shukla et al. |

FOREIGN PATENT DOCUMENTS

| | | |
|---|---|---|
| EP | 0329845 | 8/1989 |
| EP | 0690134 | 1/1996 |
| EP | 0714113 | 5/1996 |
| EP | 0989578 | 3/2000 |
| EP | 1263002 | 12/2002 |
| ES | 2725248 | 9/2019 |
| JP | 4902038 | 9/2001 |
| WO | 0103856 | 1/2001 |
| WO | 2004017688 | 2/2004 |
| WO | 2009087656 | 7/2009 |
| WO | 2010007194 | 1/2010 |
| WO | 2010138567 | 12/2010 |
| WO | 2017151139 | 9/2017 |

OTHER PUBLICATIONS

Reichardt, Empirical Parameters of Solvent Polarity as Linear Free-Energy Relationships, Angewandte Chemie International Edition, vol. 18, pp. 98-110 (1979) https://doi.org/10.1002/anie.197900981.

* cited by examiner

METHOD FOR THE MANUFACTURE OF PRECIOUS METAL ELECTRODES

CROSS-REFERENCE TO RELATED APPLICATION

This Utility patent application claims priority to German Application No. 10 2019 219 615.2 filed on Dec. 13, 2019, which is incorporated herein by reference.

TECHNICAL FIELD

One aspect belongs to the field of medical engineering and refers to a method for the manufacture of a medical electrode and to medical electrodes manufactured by the method.

BACKGROUND

WO 2010/138567 A2 describes methods for the manufacture of a medical electrode, in which either particle-containing compositions or solutions of polar platinum salts are used. However, particle-containing compositions are not really suited for inkjet applications, and/or often have to be sintered at high temperatures, making inkjet printing on temperature-sensitive surfaces impossible. Polar platinum salts are often insoluble in organic solvents. Due to their poor moistening properties, polar solvents or aqueous solutions of platinum salts are not suitable for a uniform application of a platinum-containing composition onto plastic substrates. The soluble platinum-containing compositions described must be electrochemically reduced to platinum, so that the manufacture of defined structures, for example with fine lines, is either impossible or very difficult. For these and other reason there is a need for the present embodiment.

SUMMARY

One aspect provides methods for the manufacture of a medical electrode which offers a range of technical advantages. For example, conductive structures which contain precious metals can be applied onto temperature-sensitive substrates in a simple and/or cost-efficient manner.

The object of one embodiment is to solve one or more of the problems described above and further problems incurred in prior art. The following describes embodiments by way of examples, but is not limited to these embodiments.

1. A method for the manufacture of a medical electrode, comprising the following steps:
   (i) providing a substrate;
   (ii) applying a composition onto the substrate, wherein the composition comprises
   (a) a non-aqueous solvent and
   (b) an organic precious metal complex compound that is dissolved in the solvent;
   (iii) heating the composition and thereby forming a precious metal layer on the substrate.
2. The method according to embodiment 1, wherein the solubility of the organic precious metal complex compound in propylene glycol mono-propyl ether at 25° C. and 1013 hPa is at least 1 mass percent, preferably at least 2, 3, 4, 5 or 10 mass percent, in relation to the total mass of the composition.
3. The method according to any one of the preceding embodiments, wherein the substrate comprises a metal, a ceramic or a plastic material or consists of metal, ceramic or plastic.
4. The method according to any one of the preceding embodiments, wherein the application of the composition is achieved by means of a method that is selected from the group consisting of dip coating, spraying, printing, stamping, applying with a paintbrush, applying with a brush, applying with felt, and applying with a cloth.
5. The method according to any one of the preceding embodiments, wherein the precious metal is gold, palladium or platinum.
6. The method according to any one of the preceding embodiments, wherein heating and thereby forming a precious metal layer on the substrate is carried out at a temperature of less than 1000° C., 900° C., 800° C., 700° C., 600° C., 500° C., 400° C., 300° C., 250° C., 200° C., or less than 150° C.
7. The method according to any one of the preceding embodiments, wherein the application of the composition onto the substrate is selectively achieved in the form of a predetermined pattern, with the result that the formed precious metal layer obtains the shape of the predetermined pattern.
8. The method according to any one of the preceding embodiments, wherein the substrate is a biocompatible material, preferably a biocompatible plastic material.
9. The method according to any one of the preceding embodiments, wherein the precious metal complex comprises a platinum complex of the type $[L1L2Pt[O(CO)R1]X]_n$,
   wherein L1 and L2 represent identical or different monoolefin ligands or, together, represent an L1L2 compound acting as a diolefin ligand,
   wherein X is selected from among bromide, chloride, iodide and —O(CO)R2,
   wherein —O(CO)R1 and —O(CO)R2 represent identical or different non-aromatic C8-C18 monocarboxylic acid residues or, together, represent a non-aromatic C8-C18 dicarboxylic acid residue —O(CO)R1R2(CO)O—,
   wherein these are mononuclear platinum complexes with n=1 or wherein, in the event of L1L2 and/or —O(CO)R1R2(CO)O— being present, these may be polynuclear platinum complexes with an integer n>1.
10. The method according to embodiment 9, wherein the platinum complex has the formula $[(L1L2)Pt[O(CO)R1]2]_n$, wherein n is 1 or 2, L1L2 is cyclooctadiene or norbornadiene and wherein R1 stands for a non-aromatic C7-C17 hydrocarbon residue.
11. The method according to any one of the preceding embodiments, wherein steps (ii) and (iii) are repeated one or more times to gradually build up a thicker layer of precious metal.
12. The method according to any one of the preceding embodiments, wherein step (iii) is performed above the decomposition temperature of the precious metal complex but below the melting or decomposition temperature of the substrate.
13. The method according to any one of the preceding embodiments, wherein the composition comprises an organic solvent, preferably a solvent having an ET30 value of 30 to 52 kcal/mol, 30 to 50 kcal/mol or 35 to 45 kcal/mol, further preferably a solvent selected from the group consisting of aliphatic and cycloaliphatic compounds, each with 6 to 12 carbon atoms; di-, tri- and tetrachloromethane; aromatic compounds; araliphatic compounds, such as toluol or xylol; alcohols, such as ethanol, n-propanol and isopropanol; ethers; glycol ethers, such as mono-C1-C4-alkylglycol ether and di-C1-C4-alkylglycol ether, for example ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and dipropylene glycol di-C1-C4-alkyl ether; esters having 2 to 12 carbon atoms; and ketones, such as acetone, methyl ethyl ketone, methyl isobutyl ketone and cyclohexanone, or mixtures thereof.
14. The method according to any one of the preceding embodiments, wherein the composition contains 2.5 to 25 weight percent of precious metal in relation to the total weight of the composition.
15. A medical electrode, manufactured by a method according any one of embodiments 1 to 14.
16. A use of a method according to any one of embodiments 1 to 14 for the manufacture of a medical electrode.

DETAILED DESCRIPTION

Figure 1:
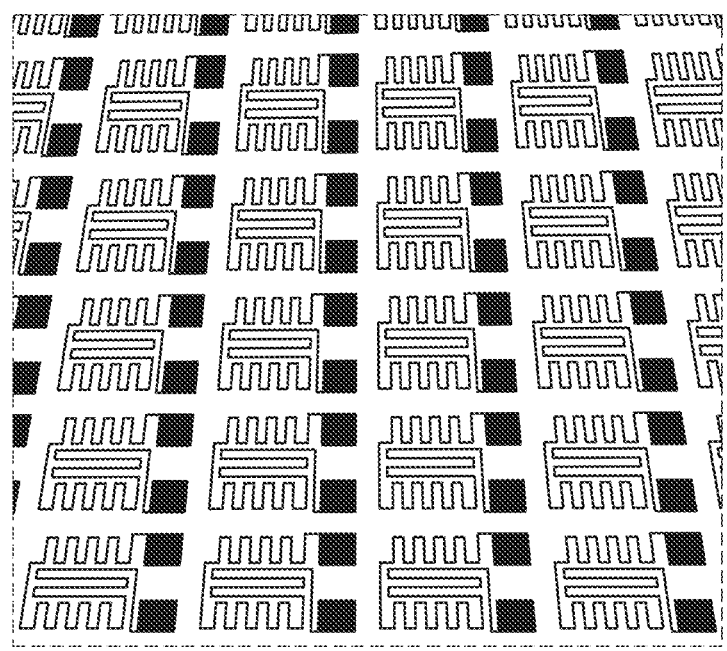
FIG. 1 illustrates an electrode structure made of platinum which is manufactured by the method according to one embodiment using inkjet printing.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

In addition to the embodiments described herein, the elements of which "have" or "comprise" a certain feature (e.g. a material), a further embodiment is always taken into consideration, in which the element in question consists of the feature alone, i.e. it does not comprise any further components. Herein, the term "comprise" or "comprising" is used as a synonym of the term "have" or "having".

If an element is used in its singular form, an embodiment is also taken into consideration in which several of these elements are present.

Unless otherwise specified or clearly excluded from the context, it is generally possible and hereby explicitly taken into consideration that features of different embodiments may also be present in the other embodiments described herein. It is likewise generally considered that all features which are described herein in connection with a method can also be used for the products described herein, for example a precious metal complex compound and a composition containing such a precious metal complex compound, and vice versa. It is only for the sake of brevity that all these considered combinations are not explicitly listed in detail in all cases. Technical solutions which are known to be equivalent to the features described herein are generally to be covered by the scope of the invention as well.

A first embodiment relates to a method for the manufacture of a medical electrode, the method comprising:
(i) providing a substrate;
(ii) applying a composition onto the substrate, wherein the composition includes
(a) a solvent (also referred to as component (A) below) and
(b) an organic precious metal complex compound (also referred to as component (B) below) that is dissolved in the solvent;
(iii) heating the composition and thereby forming a precious metal layer on the substrate.

In one embodiment, the method includes:
(i) providing a substrate;
(ii) applying a composition onto the substrate, wherein the composition includes
(a) a non-aqueous solvent and
(b) an organic precious metal complex compound that is dissolved in the solvent;
(iii) heating the composition and thereby forming a precious metal layer on the substrate, wherein the solubility of the organic precious metal complex compound in propylene glycol mono-propyl ether at 25° C. and 1013 hPa is at least 1 mass percent, in one embodiment at least 2, 3, 4, 5 or at least 10 mass percent, in relation to the total mass of the composition.

If, herein, the solubility refers to propylene glycol mono-propyl ether or another specific solvent or several different solvents, this does not necessarily mean that the composition includes this solvent or these several solvents.

In one embodiment, the precious metal complex compound is well soluble both in polar and non-polar solvents.

In one embodiment, the solubility of the organic precious metal complex compound in ethanol at 25° C. and 1013 hPa is at least 1, in one embodiment at least 2, 3, 4, 5 or at least 10 mass percent.

In one embodiment, the solubility of the organic precious metal complex compound in toluol at 25° C. and 1013 hPa is at least 1, in one embodiment at least 2, 3, 4, 5 or at least 10 mass percent.

In one embodiment, the solubility of the organic precious metal complex compound in a solvent mixture comprising eight parts of ethanol and two parts of water at 25° C. and 1013 hPa is at least 1, in one embodiment at least 2, 3, 4, 5 or at least 10 mass percent. In one embodiment, the solubility of the organic precious metal complex compound in ethanol is at least 1 mass percent and in n-hexane at least 1 mass percent.

In one embodiment, the solubility of the organic precious metal complex compound in ethanol is at least 1 mass percent and in n-hexane at least 1 mass percent.

In one embodiment, the solubility of the organic precious metal complex compound in ethanol is at least 2 mass percent and in n-hexane at least 2 mass percent.

In one embodiment, the solubility of the organic precious metal complex compound in ethanol is at least 3 mass percent and in n-hexane at least 3 mass percent.

In one embodiment, the solubility of the organic precious metal complex compound in ethanol is at least 4 mass percent and in n-hexane at least 4 mass percent.

In one embodiment, the solubility of the organic precious metal complex compound in ethanol is at least 5 mass percent and in n-hexane at least 5 mass percent.

In one embodiment, the solubility of the organic precious metal complex compound in ethanol is at least 10 mass percent and in n-hexane at least 10 mass percent.

In one embodiment, the solubility of the organic precious metal complex compound in ethanol is at least 2 mass percent and in n-hexane at least 1 mass percent.

In one embodiment, the solubility of the organic precious metal complex compound in ethanol is at least 2 mass percent and in n-hexane at least 3 mass percent.

In one embodiment, the solubility of the organic precious metal complex compound in ethanol is at least 2 mass percent and in n-hexane at least 4 mass percent.

In one embodiment, the solubility of the organic precious metal complex compound in ethanol is at least 2 mass percent and in n-hexane at least 5 mass percent.

In one embodiment, the solubility of the organic precious metal complex compound in ethanol is at least 2 mass percent and in n-hexane at least 10 mass percent.

In one embodiment, the solubility of the organic precious metal complex compound in propylene glycol mono-propyl ether is at least 1 mass percent, in ethanol at least 1 mass percent, and in n-hexane at least 1 mass percent.

In one embodiment, the solubility of the organic precious metal complex compound in propylene glycol mono-propyl ether is at least 1 mass percent, in ethanol at least 2 mass percent, and in n-hexane at least 2 mass percent.

In one embodiment, the solubility of the organic precious metal complex compound in propylene glycol mono-propyl ether is at least 1 mass percent, in ethanol at least 3 mass percent, and in n-hexane at least 3 mass percent.

In one embodiment, the solubility of the organic precious metal complex compound in propylene glycol mono-propyl ether is at least 1 mass percent, in ethanol at least 4 mass percent, and in n-hexane at least 4 mass percent.

In one embodiment, the solubility of the organic precious metal complex compound in propylene glycol mono-propyl ether is at least 1 mass percent, in ethanol at least 5 mass percent, and in n-hexane at least 5 mass percent.

In one embodiment, the solubility of the organic precious metal complex compound in propylene glycol mono-propyl ether is at least 1 mass percent, in ethanol at least 10 mass percent, and in n-hexane at least 10 mass percent.

In one embodiment, the solubility of the organic precious metal complex compound in propylene glycol mono-propyl ether is at least 1 mass percent, in ethanol at least 2 mass percent, and in n-hexane at least 1 mass percent.

In one embodiment, the solubility of the organic precious metal complex compound in propylene glycol mono-propyl ether is at least 1 mass percent, in ethanol at least 2 mass percent, and in n-hexane at least 3 mass percent.

In one embodiment, the solubility of the organic precious metal complex compound in propylene glycol mono-propyl ether is at least 1 mass percent, in ethanol at least 2 mass percent, and in n-hexane at least 4 mass percent.

In one embodiment, the solubility of the organic precious metal complex compound in propylene glycol mono-propyl ether is at least 1 mass percent, in ethanol at least 2 mass percent, and in n-hexane at least 5 mass percent.

In one embodiment, the solubility of the organic precious metal complex compound in propylene glycol mono-propyl ether is at least 1 mass percent, in ethanol at least 2 mass percent, and in n-hexane at least 10 mass percent.

In some embodiments, the organic precious metal complex compound is virtually infinitely soluble in the solvent. That means that the precious metal complex compound and the solvent can be mixed with each other at any ratio desired.

In one embodiment, the organic precious metal complex compound can be mixed, at any ratio desired, with a solvent which is selected from the group consisting of 1.5-cyclooctadiene (herein also referred to as COD), neodecanoic acid, norbornadiene and cyclohexane acid.

The solubility of the precious metal complex compound in the solvent can, for example, be determined by gradually adding, i.e. titrating, a small amount of solvent to a defined amount of the precious metal complex compound at 25° C. and 1013 hPa, until all of the solid matter has dissolved. Herein, the mixture of precious metal complex compound and solvent is continuously stirred so that it is mixed uniformly.

The solvent may be any suitable liquid substance in which the organic precious metal complex compound can be dissolved. The solvent may contain several chemical substances, i.e. the solvent may also be a solvent mixture. In one embodiment, the solvent is a non-aqueous solvent. Herein, "non-aqueous solvent" means that the solvent contains at least one liquid substance in which the organic precious metal complex compound is soluble, wherein this liquid substance is not water or an aqueous solution of inorganic substances. Thus, the solvent includes at least one substance other than water, which is liquid at 25° C. and 1013 hPa and in which the organic precious metal complex compound is soluble.

A suitable solvent can be selected based on the solubility of the precious metal complex compound in the solvent, the compatibility with the desired application method, and/or the moistening properties required with respect to the substrate. In one embodiment, the solvent itself should not result in a change in the substrate, for example a chemical reaction with the substrate, or dissolution, softening or swelling of the substrate. Suitable solvents and solvent mixtures are known in the art and can be selected by simple tests with regard to the properties mentioned above. Preferred solvents are non-polar substances, for example uncharged organic compounds. These may be pure hydrocarbons or heteroatom-containing compounds, for example heteroalkanes, heteroaromatics and heteroalkenes. Examples of organic solvents according to one embodiment comprise aliphatic and cycloaliphatic compounds, each with 6 to 12 carbon atoms; halogenated hydrocarbons, such as di-, tri- and tetrachloromethane; aromatic compounds; araliphatic compounds, such as toluol or xylol; alcohols, such as ethanol, n-propanol and isopropanol; ethers; glycol ethers, such as mono-C1-C4-alkylglycol ether and di-C1-C4-alkylglycol ether, for example ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and dipropylene glycol di-C1-C4-alkyl ether; esters having 2 to 12 carbon atoms; and ketones, such as acetone, methyl ethyl ketone, methyl isobutyl ketone and cyclohexanone. In certain embodiments, the solvent is a non-aqueous solvent which can be used for inkjet applications. In some embodiments, the solvent is compatible with the coating of plastics, for example PEEK or polyimides, which will be described in more detail below. In some embodiments, the solvent has good moistening properties with regard to plastics. In some embodiments, the solvent has a medium polarity. For example, the dipole moment of the solvent may be 1 to 10; 1 to 8; 1 to 5, or 2 to $4 \times 10^{-30}$ Cm. In one embodiment, the solvent is a protic solvent. In one embodiment, the solvent is an aprotic solvent.

In one embodiment, the ET30 value of the solvent is 30 to 52 kcal/mol, 30 to 50 kcal/mol, or 35 to 45 kcal/mol. In one embodiment, the ET30 value of the solvent is 120 to 240 kJ/mol, 125 to 220 kJ/mol, or 160 to 200 kJ/mol. The ET(30) value (herein also referred to as "ET value") of a solvent is defined as the transition energy of the longest-wave Vis/NIR absorption band in a solution with the negative solvatochromic Reichardt's dye (Betaine 30) under normal conditions in kcal/mol (REICHARDT, *Angew Chem int Ed Engl* 18, 98-110 (1979); C. REICHARDT, Solvents and Solvent Effects in Organic Chemistry Wiley-VCH, Weinheim, 2011; C. REICHARDT, Lösungsmitteleffekte in der organischen Chemie Verlag Chemie, Weinheim, 1973; all included herein in full by reference).

In one embodiment, the heating of the composition results in the decomposition of the organic precious metal complex compound, so that there is a pure precious metal layer remaining on the substrate. In one embodiment, the heating results in evaporation of the solvent. In one embodiment, the heating results in evaporation of the solvent and complete decomposition of the organic precious metal complex compound. In one embodiment, essentially no component of the composition other than the pure precious metal remains on the substrate after the composition has been heated.

Furthermore, the composition may contain an additive such as it will be described in more detail below.

The organic precious metal complex compound includes at least one central precious metal atom which is complexed by one or more organic ligands through one or more free electron pairs.

In one embodiment, the organic precious metal complex compound is soluble in a solvent, for example an organic solvent or solvent mixture, which is suitable for inkjet printing methods. To achieve this, the organic precious metal complex compound may comprise a hydrocarbon residue with 7 to 17 carbon atoms, in one embodiment 7 to 10 carbon atoms. The organic precious metal complex compound may also comprise a plurality of such hydrocarbon residues.

The organic precious metal complex compound may, for example, comprise a platinum complex of the type $[L1L2Pt[O(CO)R1]X]_n$, wherein L1 and L2 represent identical or different monoolefin ligands or, together, represent an L1L2 compound acting as a diolefin ligand, wherein X is selected from among bromide, chloride, iodide and —O(CO)R2, wherein —O(CO)R1 and —O(CO)R2 represent identical or different non-aromatic C8-C18 monocarboxylic acid residues or, together, represent a non-aromatic C8-C18 dicarboxylic acid residue —O(CO)R1R2(CO)O—, wherein these are mononuclear platinum complexes with n=1 or wherein, in the event of L1L2 and/or —O(CO)R1R2(CO)O— being present, these may be polynuclear platinum complexes with an integer n>1.

In one embodiment, the substrate may comprise a metal, a ceramic or a plastic material or consist of metal, ceramic or plastic. Examples of suitable plastic materials are, for example, PTFE, PU, ETFE, PI, PET, PE, or PEEK. The substrate may be a flat substrate, for example made of plastic, or a metal wire. Examples of polyimides are Vespel (CAS No. 62929-02-6) and Kapton (poly(4,4'-oxydiphenylene pyromellitimide). Polyimides based on biphenyl dianhydride and p-phenylene diamine (BPDA-PPD), for example PI2611 (DuPont) or U-Varnish-S (UBE), as well as polyimides based on 4,4'-oxydiphthalic anhydride and 3,4,3',4'-biphenyl tetracarboxylic acid dianhydride, such as described in U.S. Pat. Nos. 5,741,883, 6,048,959, 6,852,828 and 6,686437 (all included herein in full by reference), are characterised by good biocompatibility. Other examples are polymers which can be made of 4,4'-oxydiphthalic anhydride and 3,4,3',4'-biphenyl tetracarboxylic acid dianhydride and one of 3,4'-oxydianiline. A further example is the polymer MP-1 (M.M.A. Tech Ltd., Nahariya 2201202, Israel).

If necessary, the substrate can be cleaned and/or pretreated before the composition is applied. In one embodiment, the composition is directly applied onto the substrate, i.e., there is no other layer between the substrate and the composition. In particular, the use of adhesion promoters, such as adhesion-promoting organic substances (primers) or an additional layer of another metal, such as titanium, chromium or nickel, can be done without.

The composition may be applied using various methods, for example by dip coating, spraying, printing, stamping, applying with a paintbrush, applying with a brush, applying with felt, and applying with a cloth. Stamping also includes the methods "tampon printing" and "microcontact printing" that are known in the art.

In one embodiment, the application of the composition onto the substrate is selectively achieved in the form of a predetermined pattern, with the result that the formed precious metal layer obtains the shape of the predetermined pattern. Such a pattern may, for example, comprise elements with different process sizes which may, for example due to their respective different shapes, serve as contact elements, conductor tracks or active electrode areas for receiving or emitting an electrical signal.

To achieve this, the composition is, for example, applied using a structuring method, for example an inkjet printing method. A structuring method may comprise a selective application of the composition onto the substrate. This is referred to as bottom-up method in the art. This may be achieved, for example, by space-resolved control of an application element, such as a nozzle, or by using a mask. In one embodiment, the composition is first applied onto the entire surface and is then removed using an ablation process, such as laser ablation, to create a structured precious metal layer. This is referred to as top-down method in the art. As a matter of principle, use can be made of any bottom-up method or top-down method that is known in the art and that is suitable for applying a liquid and generating a structured precious metal layer on a substrate as described herein. In one embodiment, a plurality of structured precious metal layers are applied onto the substrate, wherein identical or different ones of the application methods described above may be used.

The composition according to one embodiment (herein also referred to as composition) may, for example, comprise the following components:

(A) 30 to 90 weight percent of at least one organic solvent,
(B) 10 to 70 weight percent of at least one platinum complex of the type $[L1L2Pt[O(CO)R1]X]_n$,
   wherein L1 and L2 represent identical or different monoolefin ligands or, together, represent an L1L2 compound acting as a diolefin ligand,
   wherein X is selected from among bromide, chloride, iodide and —O(CO)R2, wherein —O(CO)R1 and —O(CO)R2 represent identical or different non-aromatic C8-C18 monocarboxylic acid residues or, together, represent a non-aromatic C8-C18 dicarboxylic acid residue —O(CO)R1R2(CO)O—, wherein these are mononuclear platinum complexes with n=1 or wherein, in the event of L1L2 and/or —O(CO)R1R2(CO)O— being present, these may be polynuclear platinum complexes with an integer n>1, and (C) 0 to 10 weight percent of at least one additive.

If the platinum complexes are polynuclear, n generally stands for an integer, for example within the range from 2 to 5. In other words, an integer n>1 is generally in the range from 2 to 5; in particular, n will then be equal to 2 and the platinum complexes are binuclear. In particular, the L1L2 compound and the dicarboxylic acid residue —O(CO)R1R2(CO)O—, respectively, act as bridging ligands in the polynuclear platinum complexes. X can also have a bridging effect.

In one embodiment, the platinum in the platinum complexes is present in oxidation state +2.

In the composition according to one embodiment, component (B) is dissolved in component (A). If the optional component (C) is present in the composition according to one embodiment, this component (C) is also in one embodiment dissolved in component (A). In other words, if there is no optional component (C), the composition according to one embodiment is an organic solution, more precisely a true, i.e., non-colloidal organic solution; if the optional component (C) is present in the preferred form, i.e., dissolved in component (A), the same is applicable.

For example, the composition according to one embodiment may contain 30 to 90 weight percent of at least one organic solvent (A). The organic solvent(s) can be selected from a plurality of common organic solvents because the platinum complexes have good to infinite solubility in such organic solvents. It is expedient that the organic solvent or solvents is/are substantially volatile under the processing conditions of the composition according to one embodiment; in particular, this applies to the stage after application of the composition according to one embodiment onto a substrate. In general, the boiling points of the organic solvent(s) are within the range from 50 to 200° C. or higher, for example 50 to 300° C. Examples of organic solvents (A) comprise aliphatic and cycloaliphatic compounds, each with 6 to 12 carbon atoms; halogenated hydrocarbons, such as di-, tri- and tetrachloromethane; aromatic compounds; araliphatic compounds, such as toluol or xylol; alcohols, such as ethanol, n-propanol and isopropanol; ethers; glycol ethers, such as mono-C1-C4-alkylglycol ether and di-C1-C4-alkylglycol ether, for example ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and dipropylene glycol di-C1-C4-alkyl ether; esters having 2 to 12 carbon atoms; and ketones, such as acetone, methyl ethyl ketone, methyl isobutyl ketone and cyclohexanone.

For example, the composition according to one embodiment may contain 10 to 70 weight percent of at least one platinum complex of the type $[L1L2Pt[O(CO)R1]X]_n$ as component (B). For example, the platinum content of the composition according to one embodiment, which originates from the at least one platinum complex, may be within the range from 2.5 to 25 weight percent.

In a first embodiment of mononuclear platinum complexes of the type L1L2Pt[O(CO)R1]X, L1 and L2 are identical or different monoolefin ligands; X represents bromide, chloride, iodide or —O(CO)R2; and —O(CO)R1 and —O(CO)R2 represent identical or different non-aromatic C8-C18 monocarboxylic acid residues, wherein phenylacetic acid residues are in one embodiment excluded in each case.

In a second embodiment of mononuclear platinum complexes of the type L1L2Pt[O(CO)R1]X, L1 and L2 together are an L1L2 compound acting as a diolefin ligand at the same central platinum atom; X represents bromide, chloride, iodide or —O(CO)R2; and —O(CO)R1 and —O(CO)R2 represent identical or different non-aromatic C8-C18 monocarboxylic acid residues, wherein phenylacetic acid residues are in one embodiment excluded in each case.

In a third embodiment of mononuclear platinum complexes of the type L1L2Pt[O(CO)R1]X, L1 and L2 are identical or different monoolefin ligands; X represents —O(CO)R2; —O(CO)R1 and —O(CO)R2 together represent a non-aromatic C8-C18 dicarboxylic acid residue —O(CO)R1R2(CO)O— acting as a bidentate ligand at the same central platinum atom.

In a fourth embodiment of mononuclear platinum complexes of the type L1L2Pt[O(CO)R1]X, L1 and L2 together are an L1L2 compound acting as a diolefin ligand at the same central platinum atom; X represents —O(CO)R2; and —O(CO)R1 and —O(CO)R2 together represent a non-aromatic C8-C18 dicarboxylic acid residue —O(CO)R1R2(CO)O-acting as a bidentate ligand at the same central platinum atom.

In a first embodiment of binuclear or polynuclear platinum complexes of the type $[L1L2Pt[O(CO)R1]X]_n$, L1 and L2 together represent an L1L2 compound acting as a diolefin ligand bridging different platinum centres; X represents bromide, chloride, iodide or —O(CO)R2; n represents 2, 3, 4 or 5, in one embodiment 2; and —O(CO)R1 and —O(CO)R2 represent identical or different non-aromatic C8-C18 monocarboxylic acid residues, wherein phenylacetic acid residues are in one embodiment excluded in each case.

In a second embodiment of binuclear or polynuclear platinum complexes of the type $[L1L2Pt[O(CO)R1]X]_n$, L1 and L2 together represent an L1L2 compound acting as a diolefin ligand bridging different platinum centres; X represents —O(CO)R2; n represents 2, 3, 4 or 5, in one embodiment 2; and —O(CO)R1 and —O(CO)R2 together represent a non-aromatic C8-C18 dicarboxylic acid residue —O(CO)R1R2(CO)O— bridging different platinum centres.

In a third embodiment of binuclear or polynuclear platinum complexes of the type $[L1L2Pt[O(CO)R1]X]_n$, L1 and L2 represent identical or different monoolefin ligands; X represents —O(CO)R2; n represents 2, 3, 4 or 5, in one embodiment 2; and —O(CO)R1 and —O(CO)R2 together represent a non-aromatic C8-C18 dicarboxylic acid residue —O(CO)R1R2(CO)O— bridging different platinum centres.

In the composition according to one embodiment, the platinum complexes may be present in individualised but also in associated form, i.e., alone or as a mixture of several different species each of the type $[L1L2Pt[O(CO)R1]X]_n$.

By themselves, L1 and L2 are identical or different, in one embodiment identical monoolefins; together, they represent an L1L2 compound that is olefinically polyunsaturated, for example a diolefin or a polyolefin that may act as a diolefin ligand.

Examples of monoolefins comprise C2-C18 hydrocarbons with a single olefinically unsaturated double bond. These can be linear compounds, branched compounds or compounds with cyclic structures. In one embodiment, they are pure hydrocarbons; the presence of heteroatoms, for example also in the form of functional groups, is however also possible. Preferred examples of monoolefins are ethene, propene and cyclohexene.

Examples of diolefins and of compounds of the type L1L2, respectively, which are capable of acting as a diolefin ligand, comprise hydrocarbons, such as COD (1,5-cyclooctadiene), norbornadiene, COT (cyclooctatetraene) and 1,5-hexadiene. In one embodiment, these are pure hydrocarbons; the presence of heteroatoms, for example also in the form of functional groups, is however also possible. In one embodiment, L1L2 is 1,5-cyclooctadiene. In one embodiment, L1L2 is norbornadiene.

X may represent bromide, chloride, iodide or —O(CO)R2; in one embodiment, it represents chloride or —O(CO)R2, in particular —O(CO)R2.

By themselves, —O(CO)R1 and —O(CO)R2 represent identical or different non-aromatic C8-C18 monocarboxylic acid residues, wherein phenylacetic acid residues are in one embodiment excluded in each case, or together, represent a non-aromatic C8-C18 dicarboxylic acid residue of the type —O(CO)R1R2(CO)O—. The term "non-aromatic" used in this context excludes purely aromatic monocarboxylic and dicarboxylic acid residues, but not araliphatic monocarboxylic and dicarboxylic acid residues the carboxylic function(s) of which is/are bound to aliphatic carbon. In one embodiment, —O(CO)R1 and —O(CO)R2 each do not represent any phenylacetic acid residue.

Examples of non-aromatic C8-C18-monocarboxylic acids with —O(CO)R1 and —O(CO)R2 residues, respectively, comprise isomer octanoic acids including n-octanoic acid and 2-ethylhexanoic acid, the isomer nonanoic acids, and the isomer decanoic acids, to mention only a few examples. The R1 and R2 residues which are each bound to a carboxylic group comprise 7 to 17 carbon atoms, with benzylic residues being in one embodiment excluded in each case.

Examples of non-aromatic C8-C18-decarboxylic acids of the type HOOCR1R2COOH comprise appropriately substituted malonic acids, appropriately substituted 1,1-cyclobutanedicarboxylic acids, cyclohexanedicarboxylic acids, to mention only a few examples. The structural element —R1R2- which carries two carboxylic groups includes 6 to 16 carbon atoms.

Preferred examples of platinum complexes comprise [(COD)Pt[O(CO)R1]2]$_n$, wherein n is 1 or 2, and wherein R1 stands for a non-aromatic C7-C17-hydrocarbon residue, with a benzylic residue being in one embodiment excluded.

The [L1L2Pt[O(CO)R1]X]$_n$ platinum complexes can be easily prepared by exchanging ligands, in particular without using carboxylic acid salts of silver. The preparation method includes mixing and suspending, respectively, or emulsifying a two-phase system. Therein, one phase includes a reactant of the type [L1L2PtX2]$_n$ with X being selected from among bromide, chloride and iodide, in one embodiment chloride, either as such or in the form of an organic solution of such a reactant, the solution not being mixable with water at least essentially. Preferred reactants comprise [L1L2PtCl2]$_n$ with n being an integer from 1 to 5, in one embodiment with n=1. Examples of suitable organic solvents, which are mixable with water at least essentially, comprise aromatic compounds and chlorinated hydrocarbons, such as toluol, xylol, di-, tri- and tetrachloromethane, but also oxygen-containing solvents, for example corresponding ketones, esters and ethers which are not mixable with water. In contrast, the other phase includes an aqueous solution of an alkali salt (in particular sodium or potassium salt) and/or of a magnesium salt of a C8-C18-monocarboxylic acid of the type R1COOH as well as additionally of the type R2COOH where appropriate, or a corresponding alkali and/or magnesium salt of a C8-C18-dicarboxylic acid of the HOOCR1R2COOH. Which type of carboxylic acid(s) is used is based on the type of the platinum complex to be prepared or on the association of platinum complexes to be prepared. The two phases are thoroughly mixed, for example by shaking and/or stirring, while forming a suspension or emulsion. In order to maintain the suspension or emulsion state, the mixing process is, for example, carried out for a time period of 0.5 to 24 hours at a temperature within the range from 20 to 50° C. Therein, the ligands are exchanged, wherein the platinum complex(es) formed dissolve in the organic phase while the alkaliX salt or MgX$_2$ salt that has formed as well dissolves in the aqueous phase. After the step of suspending or emulsifying has been completed, the organic and the aqueous phases are separated from each other. The platinum complex(es) formed can be obtained from the organic phase and, if necessary, be subsequently cleaned using the usual methods.

For example, (COD)Pt[O(CO)CH(C$_2$H$_5$)C$_4$H$_9$]$_2$ can thus be prepared by jointly emulsifying a solution of (COD)PtCl$_2$ in dichloromethane with an aqueous solution of sodium-2-ethylhexanoate. After the emulsifying step has been completed, the saline solution therein formed by ligand exchange can be separated from the dichloromethane phase, with (COD)Pt[O(CO)CH(C$_2$H$_5$)C$_4$H$_9$]$_2$ being isolated from the latter and, if necessary, being cleaned using the usual cleaning methods. Likewise, it is for example also possible to prepare the (COD)Pt[O(CO)CH(C$_2$H$_5$)C$_4$H$_9$]Cl platinum complex provided the stoichiometry has been selected appropriately.

In addition to their aforementioned solubility in common organic solvents, the comparably low decomposition temperature of the platinum complex(es) (B), for example as low as 150° C. to 250° C., often not higher than 200° C., is an important property. This combination of properties allows using such platinum complexes as the component (B) of the composition according to one embodiment for the production of platinum layers on substrates; if used in this manner, the composition according to one embodiment represents a covering agent (coating agent), i.e., it is then prepared as a coating agent and can be used as such.

The composition according to one embodiment contains 0 to 10 weight percent, in one embodiment 0 to 3 weight percent, of at least one additive (C). As a result, the composition according to one embodiment can be free from additives or contain up to 10 weight percent of at least one additive. Examples of additives comprise moistening additives, rheology additives, defoaming agents, deaerating agents, additives to influence the surface tension, and odorous substances.

Compositions according to one embodiment can be prepared by simply mixing the components (A), (B) and, if desired, (C). Therein, the person skilled in the art selects the proportion of the components such that they correspond to the particular intended use and/or the application method used therein.

The compositions according to one embodiment can be used to produce platinum layers on substrates, in particular on temperature-sensitive substrates as well. Therein, the compositions according to one embodiment can initially be used to produce coating layers which can subsequently be subjected to thermal decomposition. During the thermal treatment, the coating layers decompose while forming platinum, i.e., the coating layers are ultimately converted into platinum layers. Therefore, one embodiment also relates to a method for the manufacture of a medical electrode, comprising the steps of:
(1) applying a coating layer from a composition according to one embodiment onto a substrate, and
(2) thermal decomposition of the coating layer under formation of a platinum layer.

The substrates to be provided with the coating layer may be substrates which comprise a great variety of materials. Therein, the substrates may comprise only one material or a plurality of materials. Among others, examples of materials comprise glass, ceramic, metal, plastic, modified or unmodified polymers of natural origin, cardboard and paper. The substrates may be provided with the coating layer on inner and/or outer surfaces or on inner and/or outer surface portions.

A first application method is dip coating. Therein, the substrate that is to be provided with the coating layer and finally with the platinum layer is dipped into and out of the composition according to one embodiment. In one embodiment, the proportion of the solvent during dip coating is within the range from 30 to 90 weight percent of the composition according to one embodiment and that of the organic precious metal complex compound within the range from 10 to 70 weight percent.

A second application method is spraying. Therein, the substrate that is to be provided with the coating layer and finally with the platinum layer, respectively, is spray coated with the composition according to one embodiment using a usual spray coating tool. Examples of spray coating tools are pneumatic spray guns, airless spray guns, rotary sprayers, or the like. In one embodiment, the proportion of the solvent during spray coating is within the range from 50 to 90 weight percent of the composition according to one embodiment and that of the organic precious metal complex compound within the range from 10 to 50 weight percent.

A third application method is printing. Therein, the substrate to be provided with the coating layer and finally with the platinum layer, respectively, is printed with the composition according to one embodiment. A preferred printing method is inkjet printing. A further preferred printing method is screen printing. In one embodiment, the proportion of the solvent during printing is within the range from 50 to 90 weight percent of the composition according to one embodiment and that of the organic precious metal complex compound within the range from 10 to 50 weight percent.

A fourth application method is application by using an application tool, for example a paintbrush, a brush, a felt, or a cloth, that is moistened with the composition according to one embodiment. Therein, the composition according to one embodiment is transferred from the application tool to the substrate to be provided with the coating layer and finally the platinum layer, respectively. With such an application method, the proportion of the solvent in one embodiment is within the range from 30 to 90 weight percent of the composition according to one embodiment and that of the organic precious metal complex compound within the range from 10 to 70 weight percent.

The coating layer that has been applied from the composition according to one embodiment and includes the at least one platinum complex of the type $[L1L2Pt[O(CO)R1]X]_n$ may first be dried and, therein, be partially or completely freed from the organic solvent before it or the dried residue is subjected to a thermal decomposition under formation of metallic platinum in the form of a layer. The thermal treatment that is performed for the purpose of thermal decomposition includes heating to an object temperature above the decomposition temperature of the at least one platinum complex. If there are several different platinum complexes of the type $[L1L2Pt[O(CO)R1]X]_n$, the person skilled in the art will select an object temperature above the decomposition temperature of the platinum complex of type (B) having the highest decomposition temperature. In general, this is done by briefly heating to an object temperature above the decomposition temperature, for example, for a period of 1 minute to 30 minutes to an object temperature within the range from 150° C. to 200° C. or from 150° C. to 250° C. or higher, for example up to 1000° C. Heating can be done especially in an oven and/or by infrared irradiation. In general, an object temperature is selected that is slightly above the respective decomposition temperature. In general, heating, or more precisely maintaining the object temperature, does not take longer than 15 minutes.

Another advantage of producing platinum layers by using the compositions according to one embodiment is that it is not necessary to use colloidal platinum or nanoplatinum-containing compositions, with the result that possible risks associated therewith can be avoided. Furthermore, in the second and third of the aforementioned application methods, clogging of the application tools, or more precisely the clogging of fine openings or nozzles of spray application tools or inkjet nozzles, can be avoided by using the composition according to one embodiment; after all, the question of drying or aggregating colloidal platinum or nanoplatinum does not arise here.

The platinum layers obtainable in this way are characterised by a high metallic gloss that is comparable to that of a mirror, provided that use is made of substrates with smooth, not too rough surfaces; the platinum layers are homogeneous in the sense of a smooth, non-granular outer surface. The thickness of the platinum layers obtainable with the method according to one embodiment may, for example, be within the range from 50 nm to 5 µm, and the platinum layers may have a two-dimensional nature with or without desired interruptions within the surface or have a desired pattern or design. The platinum layers may even be produced on temperature-sensitive substrates, i.e. for example on substrates which are not stable in their temperature above 200° C.; for example, the substrates may be temperature-sensitive polymer substrates, for example substrates based on polyolefin or polyester.

The precious metal contained in the composition may be any precious metal desired. Examples of precious metals are gold, silver, platinum, and palladium, with platinum being preferred.

After it has been applied, the composition is hardened or decomposed at an increased temperature, with the result that an elemental precious metal layer, for example a platinum layer, is formed on the substrate. This heating may be done to a temperature of less than 1000° C., 900° C., 800° C., 700° C., 600° C., 500° C., 400° C., 300° C., 250° C., 200° C. or less than 150° C. In one embodiment, the composition is heated to a temperature of 150 to 200° C. to form a precious metal layer on the substrate. In one embodiment, the composition is heated to a temperature of 200 to 250° C. to form a precious metal layer on the substrate. In one embodiment, the composition is hardened at approx. 200° C. In one embodiment, the composition is subjected to the temperature mentioned or to the aforementioned temperature range to form a precious metal layer on the substrate.

In one embodiment, step (iii) is taken above the decomposition temperature of the precious metal complex but below the melting or decomposition temperature of the substrate. Due to the decomposition of the precious metal complex, for example a platinum complex, a precious metal layer, for example a platinum layer, is formed on the substrate.

In one embodiment, the platinum complex has the formula $[(L1L2)Pt[O(CO)R1]2]_n$, wherein n is 1 or 2, L1L2 is cyclooctadiene or norbornadiene and wherein R1 stands for a non-aromatic C7-C17 hydrocarbon residue. In one embodiment, L1L2 is cyclooctadiene. In one embodiment, L1L2 is norbornadiene.

In one embodiment, steps (ii) and (iii) are repeated one or more times to gradually build up a thicker precious metal layer. To achieve this, the composition is first applied onto the substrate which has been cleaned if necessary, and is then thermally decomposed to obtain a precious metal layer as described herein. Thereafter, the composition is again applied onto the now formed precious metal layer and again thermally decomposed. Through a corresponding number of repetitions, thicker precious metal layers can be built up iteratively. In one embodiment, three-dimensional precious metal structures having almost any shape desired can be produced in this manner. For example, the precious metal layer may taper or widen in its surface (X-Y axis) in the direction away from the substrate (Z axis).

In one embodiment, step (iii) is taken above the decomposition temperature of the precious metal complex but below the melting or decomposition temperature of the substrate. This is to advantage in that the substrate and/or the precious metal structure formed thereupon do not deform or get damaged while the method is applied. The decomposition temperature is understood to mean the temperature at which the central precious metal atom is released from the precious metal complex compound.

In one embodiment, the composition includes an organic solvent, for example a solvent selected from the group consisting of aliphatic and cycloaliphatic compounds, each with 6 to 12 carbon atoms; halogenated hydrocarbons, such as di-, tri- and tetrachloromethane; aromatic compounds; araliphatic compounds, such as toluol or xylol; alcohols, such as ethanol, n-propanol and isopropanol; ethers; glycol ethers, such as mono-C1-C4-alkylglycol ether and di-C1-C4-alkylglycol ether, for example ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and dipropylene glycol di-C1-C4-alkyl ether; esters having 2 to 12 carbon atoms; and ketones, such as acetone, methyl ethyl ketone, methyl isobutyl ketone and cyclohexanone, or mixtures thereof.

In one embodiment, the composition includes glycol ether.

In one embodiment, the composition includes a Di-C1-C4-alkylglycol ether. In one embodiment, the composition includes a di-C1-C4-alkylglycol ether. In one embodiment, the composition includes a glycol ether selected from the group consisting of an ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and a dipropylene glycol di-C1-C4-alkyl ether.

In one embodiment, the composition includes a glycol ether and an alcohol.

In one embodiment, the composition includes a glycol ether and an alcohol at a weight ratio of 1:2 to 2:1. The glycol ether may, for example, be propylene glycol monopropyl ether. The alcohol may, for example, be methanol, ethanol, n-propanol, isopropanol or butanol, or a polyvalent alcohol.

In one embodiment, the organic solvent has a boiling point of 50° C. to 250° C., 50° C. to 200° C. or 100° C. to 150° C. at 1013 hPa.

In one embodiment, the composition includes 2.5 to 25 weight percent of precious metal, in one embodiment platinum, in relation to the total weight of the composition. In one embodiment, the composition comprises 5 to 20, 8 to 18 or 10 to 15 weight percent of precious metal, in one embodiment platinum, in relation to the total weight of the composition.

In one embodiment, a second electrode is applied onto the substrate. In one embodiment, a second electrode is applied onto the substrate by inkjet printing. In one embodiment, a second electrode is applied onto the substrate by inkjet printing the composition described herein. In one embodiment, an electrode is disposed as a working electrode while the second electrode is disposed as a reference electrode. In one embodiment, two electrodes are applied onto the substrate, and the two electrodes are disposed to jointly detect an electrochemical potential.

According to a further aspect of one embodiment, a medical electrode is provided, which is or can be manufactured using a method described herein. The medical electrode can be disposed for implantation, for example, in the human body. In one embodiment, the medical electrode is disposed for direct contact with tissue. In one embodiment, the medical electrode is biocompatible. In one embodiment, the medical electrode is disposed for measuring an electrochemical potential. In one embodiment, the medical electrode is disposed for measuring the blood sugar level. In one embodiment, the medical electrode is implantable and disposed for measuring the blood sugar level in the human body. The electrode may comprise a platinum layer and an enzyme, for example glucose oxidase. The electrode may comprise a plurality of parts which are disposed as measuring and reference electrode. The electrode can be disposed for emitting an electrical signal to the human body. The electrode can be disposed for receiving an electrical signal from the human body.

The electrode comprises a substrate which serves as a carrier and for supporting the precious metal layer. The electrode may comprise a flexible substrate, for example made of plastic. The substrate may, for example, be a polymer film, such as a film made of PTFE. The substrate may also be a wire, for example a metal wire. The precious metal layer may be structured and contain, for example, one or more contact elements, one or more conductor tracks and an active part which is disposed for receiving or emitting an electrical signal.

The electrical signal may be an electrochemical potential, for example an electrochemical potential which develops when blood sugar reacts with an enzyme. Further, the electrode may comprise an encapsulation. The encapsulation may consist of a biocompatible material, for example platinum, titanium or a medical silicone. The encapsulation may comprise a passage, with the result that the active part of the electrode may be led out of the encapsulation. In one embodiment, nothing but the active part of the structure protrudes from the encapsulation. The active part may comprise a part of the substrate and the precious metal layer lying thereon. The electrode may comprise a silver-containing layer. The electrode may comprise a layer of elemental silver. The electrode may comprise a layer of silver chloride. The electrode may comprise a layer of elemental silver and a layer of silver chloride.

In one embodiment, the electrode comprises a diffusion barrier which is electrically isolating and disposed for preventing any direct electrical contact between the electrode and the tissue.

In one embodiment, the electrode is or can be manufactured by an inkjet method. In one embodiment, the precious metal layer of the electrode is or can be manufactured by applying the composition according to one embodiment onto a substrate using an inkjet method.

In one embodiment, the electrode shows an activity of at least 2 µA, 3 µA, 4 µA, or at least 5 µA in a cyclic voltammetry measurement under the measurement conditions of example 7.

A further aspect of one embodiment relates to an electrochemical sensor which comprises an electrode described herein. In one embodiment, the sensor comprises a working electrode and a reference electrode. The reference electrode may comprise an enzyme, for example glucose oxidase. The enzyme may be an oxidase which is adapted to catalyse a chemical reaction of a substrate, wherein the substrate is selected from the group consisting of glucose, uric acid, ascorbic acid, citric acid, L-lactose, L-lactic acid, D-lactic acid, succinic acid, D-glucose, and ethanol. In one embodiment, the enzyme is arranged on the reference electrode in a layer having a layer thickness of approx. 10 nm to approx. 10 µm. In one embodiment, the enzyme covers 10% to approx. 100% of the surface of the reference electrode. In one embodiment, the reference electrode comprises a silver layer and a silver chloride layer. In one embodiment, the sensor comprises a diffusion barrier. The diffusion barrier may be disposed to restrict or essentially prevent the fusion of a substrate and/or a reaction product of the enzyme between the reference electrode and the working electrode. In one embodiment, the sensor is disposed to detect acetone, 3-oxobutanoic acid or (R)-3-hydroxybutyric acid.

In one embodiment, the sensor is disposed to detect an inorganic substance, for example an alkali metal, in particular sodium or potassium or ammonium.

In one embodiment, the sensor shows an activity of at least 2 µA, 3 µA, 4 µA, or at least 5 µA in a cyclic voltammetry measurement under the measurement conditions of example 7.

A further aspect of one embodiment relates to the use of a method as described herein for the manufacture of a medical electrode.

A further aspect of one embodiment relates to a solution of an organic precious metal complex compound in a solvent, the solubility of which in propylene glycol mono-propyl ether at 25° C. and 1013 hPa is at least 1, in one embodiment at least 2, 3, 4, 5, or 10 mass percent.

The solvent may be any solvent described herein. In one embodiment, the solvent is a non-aqueous solvent. In one embodiment, the ET30 value of the solvent is 30 to 52 kcal/mol, 30 to 50 kcal/mol, or 35 to 45 kcal/mol. In one embodiment, the ET30 value of the solvent is 120 to 240 kJ/mol, 125 to 220 kJ/mol, or 160 to 200 kJ/mol. If the solvent is a solvent mixture, the ET30 value refers to the solvent mixture.

In one embodiment, the solvent is suitable for inkjet printing, in one embodiment for inkjet printing on plastic or metal surfaces.

In one embodiment, the solution comprises
(a) a non-aqueous solvent (herein also referred to as component (A)) and
(b) an organic precious metal complex compound dissolved in the solvent (herein also referred to as component (B)), as described herein for the other aspects.

In one embodiment, the precious metal complex compound is well soluble both in polar and non-polar solvents.

In one embodiment, the solubility of the organic precious metal complex compound in ethanol at 25° C. and 1013 hPa is at least 1, in one embodiment at least 2, 3, 4, 5 or at least 10 mass percent.

In one embodiment, the solubility of the organic precious metal complex compound in toluol at 25° C. and 1013 hPa is at least 1, in one embodiment at least 2, 3, 4, 5 or at least 10 mass percent.

In one embodiment, the solubility of the organic precious metal complex compound in a solvent mixture including eight parts of ethanol and two parts of water at 25° C. and 1013 hPa is at least 1, in one embodiment at least 2, 3, 4, 5 or at least 10 mass percent.

In one embodiment, the solubility of the organic precious metal complex compound in ethanol is at least 1 mass percent and in n-hexane at least 1 mass percent.

In one embodiment, the solubility of the organic precious metal complex compound in ethanol is at least 1 mass percent and in n-hexane at least 1 mass percent.

In one embodiment, the solubility of the organic precious metal complex compound in ethanol is at least 2 mass percent and in n-hexane at least 2 mass percent.

In one embodiment, the solubility of the organic precious metal complex compound in ethanol is at least 3 mass percent and in n-hexane at least 3 mass percent.

In one embodiment, the solubility of the organic precious metal complex compound in ethanol is at least 4 mass percent and in n-hexane at least 4 mass percent.

In one embodiment, the solubility of the organic precious metal complex compound in ethanol is at least 5 mass percent and in n-hexane at least 5 mass percent.

In one embodiment, the solubility of the organic precious metal complex compound in ethanol is at least 10 mass percent and in n-hexane at least 10 mass percent.

In one embodiment, the solubility of the organic precious metal complex compound in ethanol is at least 2 mass percent and in n-hexane at least 1 mass percent.

In one embodiment, the solubility of the organic precious metal complex compound in ethanol is at least 2 mass percent and in n-hexane at least 3 mass percent.

In one embodiment, the solubility of the organic precious metal complex compound in ethanol is at least 2 mass percent and in n-hexane at least 4 mass percent.

In one embodiment, the solubility of the organic precious metal complex compound in ethanol is at least 2 mass percent and in n-hexane at least 5 mass percent.

In one embodiment, the solubility of the organic precious metal complex compound in ethanol is at least 2 mass percent and in n-hexane at least 10 mass percent.

In one embodiment, the solubility of the organic precious metal complex compound in propylene glycol mono-propyl ether is at least 1 mass percent, in ethanol at least 1 mass percent, and in n-hexane at least 1 mass percent.

In one embodiment, the solubility of the organic precious metal complex compound in propylene glycol mono-propyl ether is at least 1 mass percent, in ethanol at least 2 mass percent, and in n-hexane at least 2 mass percent.

In one embodiment, the solubility of the organic precious metal complex compound in propylene glycol mono-propyl ether is at least 1 mass percent, in ethanol at least 3 mass percent, and in n-hexane at least 3 mass percent.

In one embodiment, the solubility of the organic precious metal complex compound in propylene glycol mono-propyl ether is at least 1 mass percent, in ethanol at least 4 mass percent, and in n-hexane at least 4 mass percent.

In one embodiment, the solubility of the organic precious metal complex compound in propylene glycol mono-propyl ether is at least 1 mass percent, in ethanol at least 5 mass percent, and in n-hexane at least 5 mass percent.

In one embodiment, the solubility of the organic precious metal complex compound in propylene glycol mono-propyl ether is at least 1 mass percent, in ethanol at least 10 mass percent, and in n-hexane at least 10 mass percent.

In one embodiment, the solubility of the organic precious metal complex compound in propylene glycol mono-propyl ether is at least 1 mass percent, in ethanol at least 2 mass percent, and in n-hexane at least 1 mass percent.

In one embodiment, the solubility of the organic precious metal complex compound in propylene glycol mono-propyl ether is at least 1 mass percent, in ethanol at least 2 mass percent, and in n-hexane at least 3 mass percent.

In one embodiment, the solubility of the organic precious metal complex compound in propylene glycol mono-propyl ether is at least 1 mass percent, in ethanol at least 2 mass percent, and in n-hexane at least 4 mass percent.

In one embodiment, the solubility of the organic precious metal complex compound in propylene glycol mono-propyl ether is at least 1 mass percent, in ethanol at least 2 mass percent, and in n-hexane at least 5 mass percent.

In one embodiment, the solubility of the organic precious metal complex compound in propylene glycol mono-propyl ether is at least 1 mass percent, in ethanol at least 2 mass percent, and in n-hexane at least 10 mass percent.

In some embodiments, the organic precious metal complex compound is virtually infinitely soluble in the solvent. That means that the precious metal complex compound and the solvent can be mixed with each other at any ratio desired.

In one embodiment, the organic precious metal complex compound can be mixed, at any ratio desired, with a solvent which is selected from the group consisting of 1,5-cyclooctadiene (herein also referred to as COD), neodecanoic acid, norbornadiene and cyclohexane acid.

A further embodiment relates to the use of the solution to produce a precious metal layer.

A further embodiment relates to the use of the solution to produce a medical electrode.

A further aspect of one embodiment relates to a composition which comprises the following components:
(a) a non-aqueous solvent (herein also referred to as component (A)) and
(b) an organic precious metal complex compound (herein also referred to a component (B)) that is dissolved in the solvent.

In one embodiment, the solubility of the organic precious metal complex compound in propylene glycol mono-propyl ether at 25° C. and 1013 hPa is at least 1, in one embodiment at least 2, 3, 4, 5 or 10 mass percent.

In one embodiment, the solubility of the organic precious metal complex compound in ethanol at 25° C. and 1013 hPa is at least 1, in one embodiment at least 2, 3, 4, 5 or 10 mass percent.

In one embodiment, the solubility of the organic precious metal complex compound in toluol at 25° C. and 1013 hPa is at least 1, in one embodiment at least 2, 3, 4, 5 or 10 mass percent.

In one embodiment, the solubility of the organic precious metal complex compound in a solvent mixture including eight parts of ethanol and two parts of water at 25° C. and 1013 hPa is at least 1, in one embodiment at least 2, 3, 4, 5 or 10 mass percent. In one embodiment, the organic precious metal complex compound can be mixed, at any ratio desired, with a solvent which is selected from the group consisting of 1,5-cyclooctadiene (herein also referred to as COD), neodecanoic acid, norbornadiene and cyclohexane acid.

A further embodiment relates to the use of the composition to produce a precious metal layer.

A further embodiment relates to the use of the composition to produce a medical electrode.

EXAMPLES

Below, embodiments will be further illustrated by using concrete examples which, however, are not to be understood as limiting.

Example 1: Comparison Example

A test sample was applied onto polymer substrates consisting of polyimide (PI) and polyether ether ketone (PEEK) and having different layer thicknesses using printing ink based on gold nanoparticles from UT Dots (UTDAu25IJ) and having a mass concentration of 25% w/V and a dynamic viscosity of 11 cp and by using a Diamatrix inkjet printer from FujiFilm and subsequently dried in an oven. The test sample consisted of several squares having a side length of 600 μm, which were each connected in pairs by 80 μm wide and 600 μm long webs.

A 12.7 μm thick PI test substrate thus printed showed strong ink bleeding, i.e. the ink did not maintain the predetermined test structure. A surface treatment of the substrate by plasma cleaning, or by using isopropanol or acetone produced the same result. However, under the same conditions, the ink could be printed on a glass plate without the test structure changing due to ink bleeding.

When the ink, which was printed on PEEK polymer substrates using the same method, was dried at a temperature of 220° C. for 10 minutes, an electrical resistance of 2.5 MΩ to 5 MΩ was measured between two of the squares of the test sample connected by a web. This is a sign of the metal film not being formed completely. When the ink was dried a second time at 250° C. for 45 minutes, the measured resistance between the connected squares of the test sample was 7Ω to 12Ω; therein, however, the PEEK substrate deformed and shrunk.

Example 1 is described in more detail in the master thesis of David Meder (Meder, D. 2019: Herstellung and Analyse von flexiblen Polymer-Metall-Elektroden für biomedizinische Anwendungen. Masterthesis. Karlsruher Institut für Technologie (KIT)).

Example 2: Inkjet Printing on Flat Substrates

A solution of 65 mmol (COD)PtCl$_2$ in 100 ml dichloromethane was stirred, and a solution of 260 mmol sodium-2-isodecanoate in 500 ml water was added. The two-phase mixture was emulsified for 24 h at 20° C. by thorough stirring. Therein, the dichloromethane phase turned yellow.

The dichloromethane phase was separated and the solvent was distilled off. The viscous yellow residue was received in 150 ml ligroin (40-60) and the solution dried and filtered with magnesium sulfate. Then the ligroin was completely distilled off. There remained a viscous yellow residue of $(COD)Pt[O(CO)(CH_2)_5C(CH_3)_3]_2$. COD stands for cyclooctadiene.

10 g of the yellow residue were dissolved in 20 g of a solvent-additive mixture (50 weight percent of ethanol, 49.9 weight percent of propylene glycol mono-propyl ether, 0.1 weight percent of BYK-333 (surface additive from BYK). The solution that contained 10 weight percent of platinum was filled into an ink cartridge for an inkjet printer (Dimatix, Fuji-Film) as printing ink. Using CAD software (Dimatix), the sample was established for an electrode array having a resolution of 1270 dpi. The sample had a layer thickness of approx. 120 nm, a length of 100 mm and a line width of 250 µm.

Using the aforementioned printer, the electrode array was printed onto an untreated polyimide substrate (Du Pont Kapton HN). The printed polyimide substrate was hardened for 5 minutes at 200° C. in a laboratory furnace. A shiny electrically conductive electrode structure of platinum having a layer thickness of 120 nm had formed on the substrate. The finished structure is illustrated in FIG. 1.

Example 3: Coating a Wire by Felt Application

The Pt-containing solution that was used as printing ink in example 2 was applied onto two wool felts (50×50×5 mm). An SS-304 stainless steel wire with a diameter of 150 µm and a length of 1 m was manually drawn through between the two wool felts. The coated wire was hardened for 5 minutes at 200° C. in a laboratory furnace.

Example 4: Ageing Test

The electrode structure prepared in example 2 was incubated for three weeks at 67° C. in phosphate-buffered saline solution (8 g/L sodium chloride, 0.2 g/L potassium chloride, 1.15 g/L $Na_2HPO_4$ and 0.2 g/L $KH_2PO_4$; pH 7.4). According to the Arrhenius theory, this corresponds to an ageing of approx. 168 days at 37° C. (Hemmerich: Accelerated Aging—General Aging Theory and Simplified Protocol for Accelerated Aging of Medical Devices. *Medical Plastics and Biomaterials Magazine*, 1998). The samples according to one embodiment had a resistance of approx. 11 kΩ prior to ageing. Failed samples were determined by conductivity measurements. Samples with a resistance of more than 1 MΩ were assessed as failed. Comparison samples were prepared as illustrated in example 2, but printed with a printing ink based on gold nanoparticles from UTDots (UTDAu25IJ). In the comparison samples there were first failures after only two days and only half of the samples were still intact after 15 days (corresponding to 168 simulated days at 37° C.).

In the samples according to one embodiment, 100% of the samples were intact after eight days (corresponding to 68 days at 37° C.) and 90% of the samples were still intact after 15 days.

Example 5: Adhesion Test

The electrode structure prepared in example 2 and the comparison samples described in example 4 were subjected to a cross-cut test according to DIN EN ISO 2409. For this purpose, a commercially available adhesive film (Tesafilm) was stuck onto the printed platinum lines and additionally pressed on by rubbing with a fingernail. Subsequently, the adhesive film was torn off at an angle of approx. 60°. The adhesive film was examined for platinum residues (visual check). In this test, no detachment of the platinum layer could be observed in any of the samples examined.

Example 6: Preparation of a Platinum-Coated Steel Wire

The Pt-containing ink from example 2 was applied onto a steel wire (SS 304) and hardened in a laboratory furnace as described in example 2. The steel wire was put into a measurement setup and tensioned, the measurement setup consisting of the winding technology of IWT (model: FW 122) and a continuous furnace (model: Nabertherm, RHTH70/600/16). The furnace was set to a temperature of 200° C. Just before the furnace entrance the wire was clamped between two felt blocks. These were saturated with approx. 2000 µl of the Pt-containing printing ink according to example 2. During the coating process, the felt blocks were kept as saturated as possible with printing ink. The throughput speed was 0.2 m/min. A total of three layers of ink were applied and hardened, with one hardening step after each application step.

Example 7: Electrochemical Properties

Figure 3:
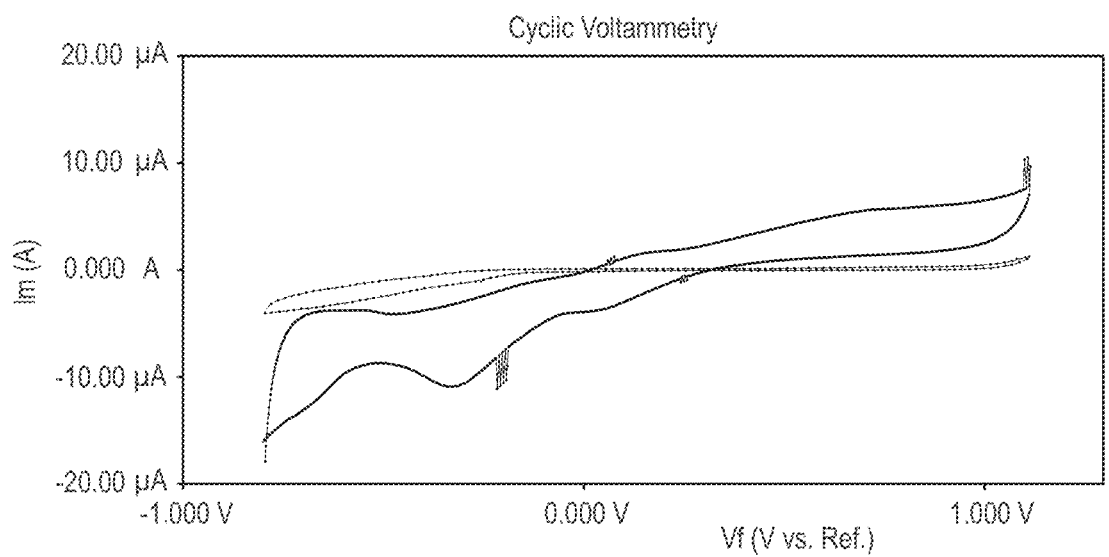
FIG. 3 illustrates a cyclic voltammetry measurement of an SS-304 stainless steel wire (dotted line) and a wire coated with platinum using the method according to one embodiment (continuous line).
Figure 4:
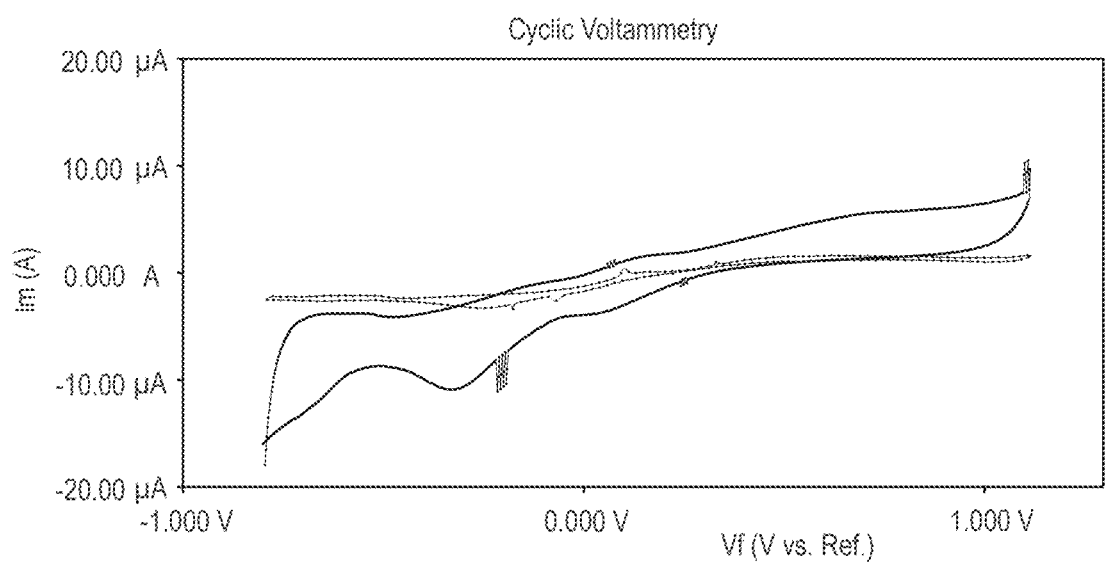
FIG. 4 illustrates a cyclic voltammetry measurement of a drawn platinum wire (dotted line) and a wire coated with platinum using the method according to one embodiment (continuous line).

A steel wire, a drawn platinum wire, and a steel wire coated with platinum using the method according to one embodiment were subjected to cyclic voltammetry by using the Gamry Interface 1010 B potentiostat. At first, the wires were cleaned for 5 minutes in 99% isopropanol in an ultrasonic bath. Thereafter, they were contacted and cyclic voltammetry was carried out with the following measurement setup: counter electrode: platinum; reference electrode: calomel electrode; electrolyte: 1 mM $H_2O_2$ solution; scan limit: −0.8 V to 1.1 V, scan rate: 100 mV/s, 5 cycles; electrode surface: 0.300 $mm^2$. The platinum-coated steel wire showed an oxidation activity that was about 3.3 times higher than that of the drawn Pt wire (at 690 mV: drawn wire: 1.65 µA; coated wire: 5.44 µA; see FIG. 4). The bare steel wire showed almost no activity (205 nA) during oxidation (see FIG. 3), so it can be excluded that the base material has a significant influence on the measurement.

Figure 2:
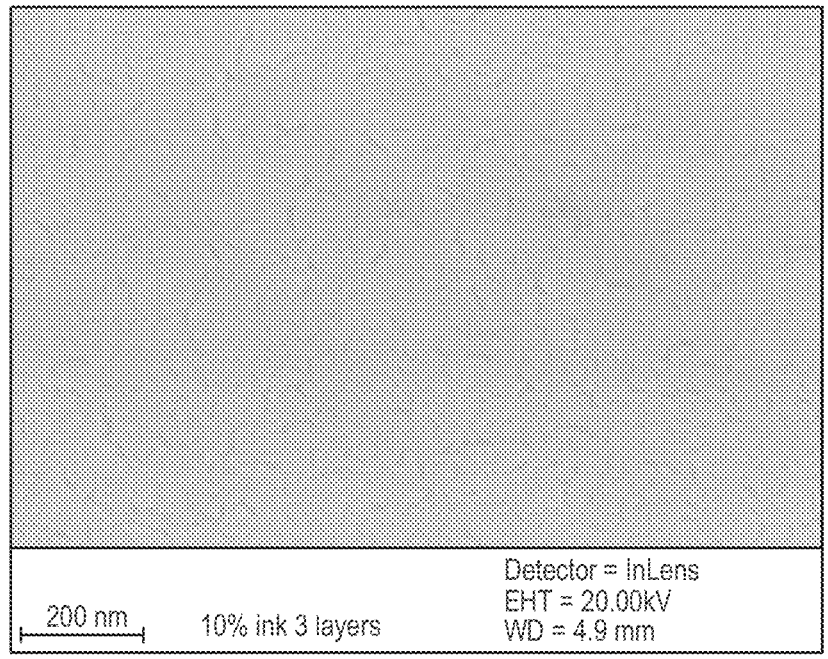
FIG. 2 illustrates a scanning electron micrograph of a wire coated with platinum using the method according to one embodiment.

In SEM examinations, the platinum-coated wire showed a nanoporous structure which may be responsible for the increased activity. An image of this structure is illustrated in FIG. 2.

Such a Pt-coated steel wire thus provides a better signal-to-noise ratio at the same voltage and/or it can be measured at the same sensitivity with a lower electrical voltage, with the result that the energy consumption of a sensor including an electrode according to one embodiment can be reduced.

Example 8: Cleanliness of the Precious Metal Layer 1 mL ink according to example 2 was dripped onto a substrate of aluminium oxide. Due to the thick layer, the platinum could be easily lifted off. The platinum flakes did not contain any components that were volatile above 200° C.

The platinum flakes were subjected to thermal analysis using the NETZSCH TG 209F1 Libra TGA209F1D-0066-L measuring instrument in a temperature range from 25° C. to 800° C. at a heating rate of 5.0 K/minute. The measurement was evaluated with NETZSCH Proteus Software to determine the loss of mass of the sample. No loss of mass was detected in the sample within the scope of the measuring accuracy. This result shows that a clean precious metal layer is formed by the method according to one embodiment, the layer being free from foreign substances with a decomposition temperature of up to 800° C.

Example 9: Solubility of the Precious Metal Layer

The compound $(COD)Pt[O(CO)(CH_2)_5C(CH_3)_3]_2$ that was synthesised as described in example 2 and contains 32.33 mass percent of platinum was dissolved at different proportions in the following solvents:
Ligroin 40/60
Toluol
Propylene glycol mono-propyl ether
Ethanol This showed an essentially unlimited solubility or mixability of the precious metal complex in each of the solvents mentioned above.

The above mentioned precious metal complex compound could be completely dissolved in a solvent mixture of 8 g ethanol and 2 g water in a proportion of 50 weight percent in relation to the total mass of the solution. The solution was clear and did not contain any visible solid parts or particles. This corresponds to a content of platinum of approx. 15 mass percent in relation to the total mass of the solution.

Example 9A 0.90 g of a complex of platinum and the ligands 1,5-cyclooctadiene and 2-ethylhexanoate were each stirred with 0.10 g of a solvent (according to Table 1) for 2 h until a homogeneous, clear solution was obtained. When the solvent evaporated, the solution remained clear for each of the solvents mentioned in Table 1 in every concentration—no turbidity, precipitation or crystallisation was observed.

TABLE 1

Solvents used in example 9A and their $E\tau(30)$ values according to REICHARDT, *Angew Chem Int Ed Engl* 18, 98-110 (1979).

| Solvent | $E\tau(30)$ value [kcal/mol] |
| --- | --- |
| Ethanol | 51.9 |
| 1-Propanol | 48.6 |
| 2-Propanol | 41.1 |
| Dichloromethane | 50.7 |
| Diethylene glycol diethyl ether | 37.9 |
| n-Octane | 31.1 |
| n-Hexane | 30.9 |

Example 9B 0.90 g of a complex of platinum and the ligands 1,5-cyclooctadiene and 2-ethylhexanoate were stirred with 0.10 g of a mixture consisting of 80% ethanol and 20% water ($E\tau(30)=53.7$ kcal/mol) for 2 h. The result was a solution which became cloudy as soon as the solvent evaporated.

Example 9C 0.90 g of a complex of platinum and the ligands 1,5-cyclooctadiene and 2-ethylhexanoate were stirred with 0.10 g water ($E\tau(30)=63.1$ kcal/mol) for 2 h. The phases remained separated.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A method for the manufacture of a medical electrode, comprising:
    (i) providing a substrate;
    (ii) applying a composition onto the substrate, wherein the composition comprises:
        (a) a non-aqueous solvent and
        (b) an organic precious metal complex compound that is dissolved in the solvent;
    (iii) heating the composition and thereby forming a precious metal layer on the substrate;
        wherein the precious metal is gold, palladium or platinum and wherein the medical electrode is biocompatible such that it is configured for implantation within a human body and for direct contact with tissue therein;
        wherein the solubility of the organic precious metal complex compound in propylene glycol mono-propyl ether at 25° C. and 1013 hPa is at least 1 mass percent in relation to the total mass of the composition;
        wherein the precious metal complex comprises a platinum complex of the type [L1L2Pt[O(CO)R1]X]n,
        wherein L1 and L2 represent identical or different monoolefin ligands or, together, represent an L1L2 compound acting as a diolefin ligand,
        wherein X is selected from among bromide, chloride, iodide and —O(CO)R2,
        wherein —O(CO)R1 and —O(CO)R2 represent identical or different non-aromatic C8-C18 monocarboxylic acid residues or, together, represent a non-aromatic C8-C18 dicarboxylic acid residue —O(CO)R1R2(CO)O—, and
        wherein these are mononuclear platinum complexes with n=1 or wherein, in the event of L1L2 and/or —O(CO)R1R2(CO)O— being present, these may be polynuclear platinum complexes with an integer n≥1.

2. The method according to claim 1, wherein the solubility of the organic precious metal complex compound in propylene glycol mono-propyl ether at 25° C. and 1013 hPa is at least one of 2, 3, 4, 5, or 10 mass percent, in relation to the total mass of the composition.

3. The method according to claim 1, wherein the substrate comprises a metal, a ceramic or a plastic material or consists of metal, ceramic or plastic.

4. The method according to claim 1, wherein the application of the composition is achieved by using a method that is selected from the group consisting of dip coating, spraying, printing, stamping, applying with a paintbrush, applying with a brush, applying with felt, and applying with a cloth.

5. The method according to claim 1, wherein the heating and thereby forming of a precious metal layer on the substrate is carried out at a temperature of less than 1000° C., 900° C., 800° C., 700° C., 600° C., 500° C., 400° C., 300° C., 250° C., 200° C., or less than 150° C.

6. The method according to claim 1, wherein the application of the composition onto the substrate is selectively achieved in the form of a predetermined pattern, with the result that the formed precious metal layer obtains the shape of the predetermined pattern.

7. The method according to claim 1, wherein the substrate is a biocompatible plastic material.

8. The method according to claim 1, wherein the platinum complex has the formula $[(L1L2)Pt[O(CO)R1]_2]_n$, wherein n is 1 or 2, L1L2 is cyclooctadiene or norbornadiene and wherein R1 represents a non-aromatic C7-C17 hydrocarbon residue.

9. The method according to claim 1, wherein (ii) and (iii) are repeated one or more times to gradually build up a thicker layer of precious metal.

10. The method according to claim 1, wherein (iii) is performed above the decomposition temperature of the precious metal complex but below the melting or decomposition temperature of the substrate.

11. The method according to claim 1, wherein the composition comprises an organic solvent having an ET30 value of 30 to 52 kcal/mol, 30 to 50 kcal/mol or 35 to 45 kcal/mol selected from the group consisting of aliphatic and cycloaliphatic compounds, each with 6 to 12 carbon atoms; di-, tri- and tetrachloromethane; aromatic compounds; araliphatic compounds, such as toluol or xylol; alcohols, such as ethanol, n-propanol and isopropanol; ethers; glycol ethers, such as mono-C1-C4-alkylglycol ether and di-C1-C4-alkylglycol ether, for example ethylene glycol mono-C1-C4-alkyl ether, ethylene glycol di-C1-C4-alkyl ether, diethylene glycol mono-C1-C4-alkyl ether, diethylene glycol di-C1-C4-alkyl ether, propylene glycol mono-C1-C4-alkyl ether, propylene glycol di-C1-C4-alkyl ether, dipropylene glycol mono-C1-C4-alkyl ether, and dipropylene glycol di-C1-C4-alkyl ether; esters having 2 to 12 carbon atoms; and ketones, such as acetone, methyl ethyl ketone, methyl isobutyl ketone and cyclohexanone, or mixtures thereof.

12. The method according to claim 1, wherein the composition contains 2.5 to 25 weight percent of precious metal in relation to the total weight of the composition.

13. Manufacturing a medical electrode using the method according to claim 1.

* * * * *